(12) United States Patent
Janssen et al.

(10) Patent No.: US 8,454,360 B2
(45) Date of Patent: Jun. 4, 2013

(54) LIQUID DROPLET INTERPROXIMAL CLEANING APPARATUS WITH GAS STREAM PROTECTION

(75) Inventors: Jozef Johannes Maria Janssen, Herten (NL); Bart Gottenbos, Budel (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 13/126,497

(22) PCT Filed: Oct. 30, 2009

(86) PCT No.: PCT/IB2009/054828
§ 371 (c)(1),
(2), (4) Date: Apr. 28, 2011

(87) PCT Pub. No.: WO2010/055433
PCT Pub. Date: May 20, 2010

(65) Prior Publication Data
US 2011/0217671 A1    Sep. 8, 2011

Related U.S. Application Data

(60) Provisional application No. 61/115,181, filed on Nov. 17, 2008.

(51) Int. Cl.
*A61C 3/02* (2006.01)
(52) U.S. Cl.
USPC .......................................................... 433/88
(58) Field of Classification Search
USPC ................. 433/80, 81, 88, 89; 601/162, 163
See application file for complete search history.

(56) References Cited

U.S. PATENT DOCUMENTS

| 4,149,315 A | 4/1979 | Page, Jr. et al. |
| 5,593,304 A | 1/1997 | Ram |
| 5,658,144 A | 8/1997 | Tinder et al. |
| 5,820,373 A * | 10/1998 | Okano et al. ..................... 433/80 |
| 5,853,128 A * | 12/1998 | Bowen et al. ................. 239/329 |
| 6,923,007 B1 | 8/2005 | Markham et al. |
| 2005/0272002 A1* | 12/2005 | Chenvainu et al. ............. 433/80 |

FOREIGN PATENT DOCUMENTS

| EP | 1911465 A1 | 4/2008 |
| GB | 208791 | 12/1923 |
| WO | 2008001303 A1 | 1/2008 |
| WO | 2008012707 A2 | 1/2008 |

* cited by examiner

*Primary Examiner* — Cris L Rodriguez
*Assistant Examiner* — Eric Rosen

(57) ABSTRACT

The interproximal cleaning apparatus includes a gas reservoir (12) containing a compressed gas, such as $CO_2$, in both liquid and gaseous states. A siphon tube (20) extends down into the liquid region of the gas reservoir when the apparatus is in an upright position. The siphon tube connects the reservoir to a metering valve (18) which has a metered volume to accommodate an amount of liquid compressed gas which is sufficient for good liquid droplet cleaning when it decompresses and forms a gaseous stream, without damage to the dental regions of the user. If the apparatus is severely tilted or turned upside down, gaseous $CO_2$ or a combination of gaseous and liquid $CO_2$ will enter the siphon tube and then the metering valve. The size of the metering valve will limit the volume of the gaseous $CO_2$ to a safe amount, both when liquid $CO_2$ or gaseous $CO_2$ are applied to the metering valve.

10 Claims, 1 Drawing Sheet

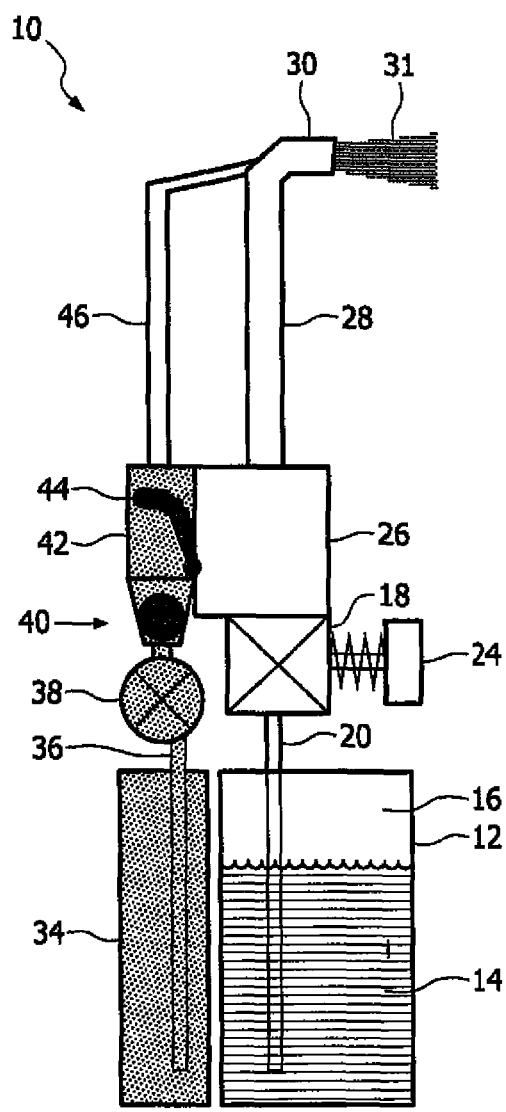

LIQUID DROPLET INTERPROXIMAL CLEANING APPARATUS WITH GAS STREAM PROTECTION

TECHNICAL FIELD

This invention relates generally to interproximal (interdental) cleaning apparatus/appliances, and more particularly concerns such an apparatus designed to protect against unsafe increases in gas stream and/or liquid droplet flow due to orientation of the apparatus in use.

BACKGROUND OF THE INVENTION

Liquid droplet interproximal (interdental) cleaning apparatus/appliances use a $CO_2$ or other gas stream to accelerate a volume of liquid and to produce liquid droplets therefrom, which are directed to the dental regions for cleaning. A $CO_2$ gas stream is typically produced by the rapid expansion of a small amount of gaseous $CO_2$ released from a $CO_2$ reservoir, such as a cartridge.

The $CO_2$ reservoir will typically include both liquid $CO_2$ and gaseous $CO_2$. Typically, only gaseous $CO_2$ proceeds from the reservoir when the apparatus is in an upright orientation. The gaseous $CO_2$ is directed into and then exits from a metered valve to form a gas stream.

A portion of the gas stream may be used to accelerate liquid from the reservoir into the gas stream to produce liquid droplets. However, when the apparatus is tilted, including below horizontal or even completely upside down, liquid $CO_2$ enters the metered valve instead of gaseous $CO_2$, which results in a significant increase in the amount of gas from the metered valve as the gas decompresses prior to and at the exit of the valve. This can result in the speed of the modified gas stream being excessive and/or the fluid being accelerated at a too high a rate, resulting ultimately in damage to the gingival or interproximal pockets of the dental region.

Hence, it is desirable to have a structural arrangement which protects against increases in the decompressing (expanding) gas from the gas reservoir, regardless of the orientation of the apparatus.

SUMMARY OF THE INVENTION

Accordingly, an interdental cleaning apparatus is described herein, comprising: a compressed gas reservoir, containing liquid compressed gas and gaseous compressed gas; a liquid reservoir; a system for moving liquid in the liquid reservoir out of the liquid reservoir and into contact with an output gaseous stream of gas from the decompression of gas from the gas reservoir, resulting in a stream of fluid droplets which can be directed from the apparatus toward the dental regions of a user for cleaning thereof; and a metering valve and a siphon tube extending from the metering valve to the gas reservoir, wherein the metering valve has such a metered volume that the output of gaseous gas resulting from the decompression of gas from the gas reservoir will not damage the dental regions of the user, regardless of the orientation of the apparatus in use.

BRIEF DESCRIPTION OF THE DRAWINGS

The drawing is a schematic view of a liquid droplet dental cleaning apparatus, incorporating the gas limiting system described herein.

BEST MODE FOR CARRYING OUT THE INVENTION

The FIGURE shows in general a fluid droplet interproximal cleaning apparatus, generally at 10. In the embodiment shown, the apparatus includes a gas reservoir 12, which can be in the form of a $CO_2$ cartridge. The $CO_2$ cartridge will typically include both liquid $CO_2$, shown at 14, and gaseous $CO_2$, shown at 16, for example. Connecting the reservoir 12 to a metering valve 18 is a siphon tube 20, which is described in more detail below.

The metering valve is operated by a control button or similar element 24, which allows a selected amount of $CO_2$ into a gas chamber 26. The selected amount of gas will typically be appropriate for a single use, for example in the range of 0.01 ml. Extending from gas chamber 26 and forming a part of a nozzle for the apparatus is a gas streaming line 28, which terminates in an exit orifice 30.

The interdental cleaner also includes a reservoir for liquid 34, which could be water or some other solution, including mouthwash or various oral care treatment solutions. Pump 38 moves liquid through a connecting tube 36 from reservoir 34 to a one-way valve 40 and then to a liquid chamber 42. Liquid chamber 42 is adapted to contain a single use of liquid, which in the embodiment shown is approximately 0.1 ml.

A one-way valve 44 connects gas chamber 26 to liquid chamber 42. A liquid line 46 extends from liquid chamber 42 and delivers liquid to gas line 28, near the exit orifice 30 in the embodiment shown.

In operation, the expanding gas from the gas reservoir will create sufficient pressure in gas chamber 26 to open one-way valve 44. Gas enters chamber 42 and acts on the liquid therein, accelerating the liquid through liquid line 46 to the gas stream in the gas line 28. Typically, only a small amount of gas is necessary to produce this liquid acceleration effect.

When the accelerated liquid comes into contact with the gas stream, liquid droplets are produced in a desired size range and with a desired velocity, such as 10 microns in diameter, with a velocity of 60 mls. The stream of fluid droplets (31) proceeds through the exit orifice 30 to the dental region to be cleaned, such as the interproximal areas of the teeth.

Siphon tube 20 extends down into gas reservoir 12 a sufficient distance (usually a short distance from the bottom) that only liquid $CO_2$ (or other gas) can enter metering valve 18 when the apparatus is in an upright orientation. The size of the metering valve is such as to accommodate a single use of $CO_2$ from the reservoir (as it expands) when the $CO_2$ from the reservoir is in a liquid state. When the apparatus is tilted or used upside down, however, $CO_2$ in a gaseous state will now enter the siphon tube, instead of liquid $CO_2$, since the upper end of the gas reservoir, where the siphon tube terminates, contains gaseous $CO_2$. This will result in a smaller amount of $CO_2$ in the metering valve and the gas chamber because of the lower density of gaseous $CO_2$ compared to liquid $CO_2$, i.e. $CO_2$ will expand less when the $CO_2$ from the reservoir is in a compressed gaseous state than when it is in a compressed liquid state.

The arrangement of the siphon tube and the volume of the metering valve is such that in normal upright operation, liquid $CO_2$ having a volume of the metering valve results in the correct amount of $CO_2$ gas to produce an effective single use of the cleaning apparatus, while in a tilted or upside down position, a lesser volume of $CO_2$ gas is produced since the gas from the reservoir is in a gaseous state already. This lower volume of $CO_2$ gas, due to the small volume of the metering valve, ensures the safety of operation of the apparatus, regardless of the orientation of the apparatus.

However, the siphon tube 20 will function as a small reservoir when the apparatus is upside down, resulting in several rapid bursts or shots of $CO_2$ in succession, as the gaseous $CO_2$ moves into the metering valve, in order to accomplish the desired cleaning action, but without any risk of excessive gas stream or liquid droplet velocity.

Hence, the siphon tube and the valve are configured and arranged so that a tilted or upside down orientation will not result in an increase of $CO_2$ gas stream output beyond a safe level, for instance, the level of $CO_2$ output when the apparatus is in an upright position. This safety arrangement involves both the dimensions and position of the siphon tube in the gas reservoir and the volume of the metering valve, which is set to that volume associated with safe gas stream characteristics for the liquid $CO_2$ from the gas reservoir and its resulting expansion as it is released from the reservoir.

Accordingly, a fluid droplet interdental cleaning arrangement has been described which provides protection for the user, regardless of the orientation of the apparatus.

Although a preferred embodiment of the invention has been disclosed for the purposes of illustration, it should be understood that various changes, modifications and substitutions may be incorporated in the embodiment without departing from the spirit of the invention, which is defined by the claims which follow.

The invention claimed is:

1. A hand-held fluid droplet interproximal dental cleaning apparatus, comprising:
   a container source of compressed gas (12) containing gas in a liquid state (14) and gas in a gaseous state (16);
   a siphon tube (20) extending down into the container source of compressed gas far enough that an open end of the siphon tube will be in a region of the container containing gas in a liquid state when the apparatus is in an upright position;
   a metering valve (18) adapted to receive a selected volume of compressed gas from the container source, wherein the metering valve is limited in size to a single use of gas in a liquid state, approximately 0.01 ml, which results in an output stream of expanding decompressed gas for a single use of operation of the cleaning apparatus;
   a gas chamber (26) into which the decompressed gas from the metering valve is directed, wherein the decompressed gas allowed into the gas chamber is limited to said decompressed gas from the metering valve;
   a reservoir source of liquid (34);
   a system (38, 40) for moving liquid in the liquid reservoir in one direction into a liquid chamber (42) which is separate from the reservoir and adapted to contain a single use of liquid, approximately 0.1 ml;
   a one-way valve (44) connecting the gas chamber to the liquid chamber, wherein in operation pressure in the gas chamber produced by the decompressed gas opens the one-way valve so that an amount of the decompressed gas moves into the liquid chamber, accelerating the liquid therein through a fluid connecting line (46) to contact the stream of decompressed gas; and
   a gas stream line (28) extending from the gas chamber, wherein interaction of the liquid from the liquid chamber and the stream of decompressed gas in the gas stream line produces fluid droplets (31) which are directed out of the apparatus to a desired dental surface.

2. The cleaning apparatus of claim 1, wherein the apparatus further comprises a pump (38) for moving the liquid in the liquid reservoir into the liquid chamber.

3. The cleaning apparatus of claim 1, including a user-operated control member (24) for the metering valve.

4. The cleaning apparatus of claim 1, wherein the open end of the siphon tube is in a region of the container containing gas in a gaseous state when the apparatus is in a tilted or upside down orientation.

5. The cleaning apparatus of claim 4, wherein the siphon tube is configured so as to contain sufficient gas for a dental cleaning use of the apparatus when the apparatus is in a tilted or upside down orientation.

6. An interdental cleaning apparatus, comprising:
   a compressed gas reservoir (12), containing liquid compressed gas and gaseous compressed gas;
   a liquid reservoir (34);
   a liquid chamber (42) which is separate from the liquid reservoir and adapted to contain a single use of liquid of approximately 0.1 ml;
   a system (38, 40, 42, 44, 46) for moving liquid in the liquid reservoir out of the liquid reservoir into the liquid chamber and from there into contact with an output stream of gaseous gas from the decompression of gas from the gas reservoir, resulting in a stream of fluid droplets (31) which can be directed from the apparatus toward the dental regions of a user for cleaning thereof; and
   a metering valve (18) and a siphon tube (20) extending from the metering valve to the gas reservoir, wherein the metering valve is limited in size to a single use of gas, approximately 0.01 ml, wherein the single use of gas creates the output stream of gaseous gas, wherein the output stream of gaseous gas resulting from the decompression of gas from the gas reservoir and the resulting stream of droplets results in a cleansing effect on the dental regions of the user, regardless of the orientation of the apparatus in use.

7. The cleaning apparatus of claim 6, wherein the siphon tube extends down into the gas reservoir sufficiently that only liquid gas enters the siphon tube when the apparatus is in an upright position.

8. The cleaning apparatus of claim 7, wherein the siphon tube is arranged relative to the gas reservoir such that when the cleaning apparatus is tilted or upside down, gaseous gas from the gas reservoir will enter the siphon tube.

9. The cleaning apparatus of claim 8, wherein the siphon tube is configured so as to contain sufficient gaseous gas for a single cleaning use of the apparatus when the cleaning apparatus is tilted or upside down.

10. The cleaning apparatus of claim 6, wherein the compressed gas is $CO_2$.

* * * * *